United States Patent [19]

Wagnon et al.

[11] Patent Number: 4,806,655
[45] Date of Patent: Feb. 21, 1989

[54] PROCESS FOR THE STEREOSPECIFIC SYNTHESIS OF INDOLE DERIVATIVES

[75] Inventors: Jean Wagnon, Montpellier; Claude Plouzane, Saint Georges d'Orques; Bernard Tonnerre, Vailhauques; Dino Nisato, Saint Georges d'Orques, all of France

[73] Assignee: Societe Anonyme: Sanofi, Paris, France

[21] Appl. No.: 67,273

[22] Filed: Jun. 29, 1987

[30] Foreign Application Priority Data

Jul. 3, 1986 [FR] France ................................. 86 09680

[51] Int. Cl.$^4$ .................... C07B 53/00; C07D 209/16;
C07D 403/12; C07D 405/12
[52] U.S. Cl. ...................................... 548/455; 548/231;
548/507; 548/467
[58] Field of Search ................................ 548/455, 507

[56] References Cited

U.S. PATENT DOCUMENTS

| | | | |
|---|---|---|---|
| 4,234,595 | 1/1980 | Kreighbaum | 548/507 |
| 4,404,217 | 9/1983 | Demarne | 548/504 |
| 4,510,315 | 4/1985 | Demarne | 548/455 |
| 4,522,824 | 6/1985 | Wagnon | 548/455 |

OTHER PUBLICATIONS

Schwender, J. Med Chem 13, 634 (1970).

*Primary Examiner*—Mark L. Berch
*Attorney, Agent, or Firm*—Foley & Lardner, Schwartz, Jeffery, Schwaab, Mack, Blumenthal & Evans

[57] ABSTRACT

The present invention relates to a process for the stereospecific synthesis of indole derivatives of formula:

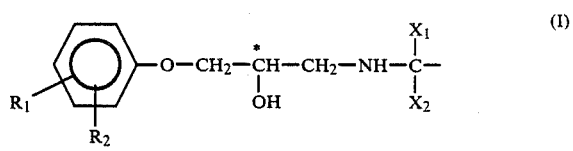

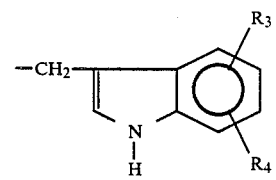

which consists in using 3-tosyloxy-1,2-O-isopropylidenepropane-1,2-diol (II) in an optically pure form in order to introduce the asymmetric carbon C* of compound (I). Compound (II) is condensed with a suitable primary amine in order to prepare an oxazolidinone and condensation with a suitable phenol, and the oxazolidinone ring is then opened to form an indole compound (I).

11 Claims, No Drawings

PROCESS FOR THE STEREOSPECIFIC SYNTHESIS OF INDOLE DERIVATIVES

The present invention relates to a process for the asymmetrical synthesis of optically pure indole derivatives corresponding to the formula:

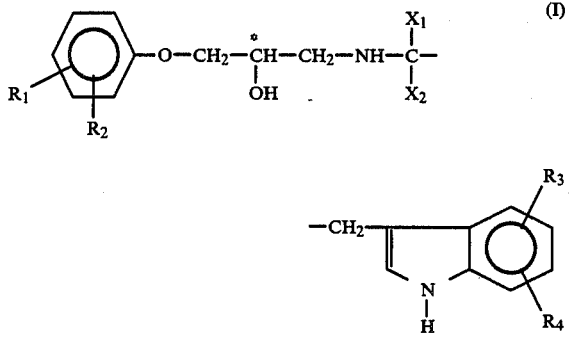

in which:
the C* atom has the (R) or (S) configuration;
$X_1$ and $X_2$ each independently denote a hydrogen atom or a lower alkyl;
$R_1$ and $R_2$ each independently denote a hydrogen atom, a halogen atom, a lower alkyl, a lower alkoxy or a formyl, or $R_1$ and $R_2$, taken together with the benzene nucleus to which they are bonded, form an optionally substituted bicyclic nucleus such as:

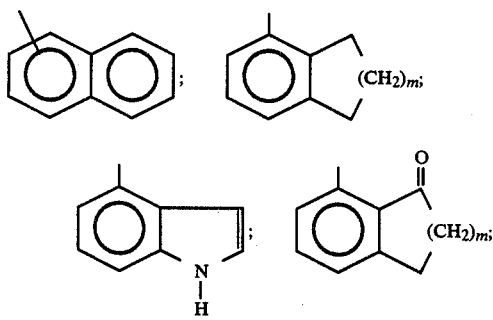

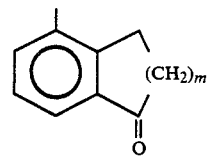

$R_3$ and $R_4$ each independently denote a hydrogen atom, a halogen atom, a lower alkyl or a lower alkoxy; and m represents an integer between 1 and 3.

If $X_1$ is different from $X_2$, (I) can have one of the following configurations: (R,R), (R,S), (S,R) or (S,S).

In the present description and in the claims which follow, the term "lower alkyl" is understood as meaning a linear or branched alkyl containing from 1 to 4 carbon atoms, and the term "lower alkoxy" is understood as meaning a hydroxyl group substituted by a lower alkyl such as defined above. The symbol C* denotes an asymmetric carbon.

The indole derivatives (I) obtained by the process according to the invention are compounds which act on the cardiovascular system. These compounds are useful in the preparation of drugs for the treatment of cardiovascular complaints. It is known that the pharmacological activity of compounds such as (I) varies according to the isomer studied. Thus, for propranolol, the results are reported in "Pharmacology of Antihypertension Drugs", A. SCRIABINE, Raven Press, 1980, p. 197.

The compounds prepared by the process according to the invention were tested by their α and β-adrenergic effects. Thus, S(−)-3-(1,1-dimethyl-2-(indol-3-yl)ethylamino)-1-(indol-4-yloxy)propan-2-ol hydrochloride was found to have α, $β_1$ and $β_2$-adrenergic effects superior to those of R(+)-3-(1,1-dimethyl-2-(indol-3-yl)ethylamino)-1-(indol-4-yloxy)propan-2-ol hydrochloride.

The process of synthesis according to the invention is stereospecific on the carbon carrying the alcohol functional group.

European Pat. No. 25 727, French Pat. No. 2 523 964 and U.S. Pat. No. 4,314,943 describe a process for the synthesis of a mixture of stereoisomers of certain compounds (I') by condensing an epoxide with an amine:

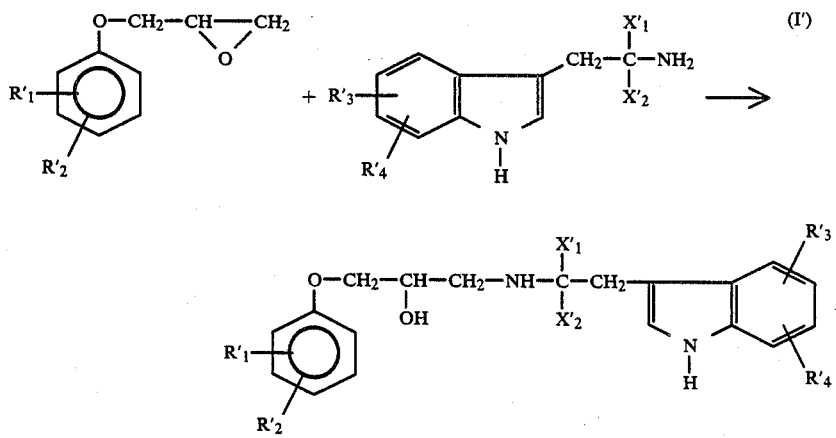

By this process of synthesis, the compounds (I') are obtained in the form of a mixture of 2 optical isomers if $X'_1=X'_2$, or a mixture of 4 stereoisomers if $X'_1$ and $X'_2$ have different meanings. Separation of each of the optical isomers requires the application of apprpriate physical or chemical methods, which lengthen the process and reduce the yield of optically pure product.

According to the present invention, it has now been found possible to prepare the indole derivatives (I) by a process of stereospecific synthesis on the carbon carrying the alcohol functional group.

In the description and in the examples below, the following abbreviations will be used:
Boc: tert.-butoxycarbonyl
$(Boc)_2O$ tert.-butoxycarbonic anhydride
THF: tetrahydrofuran
DMF: dimethylformamide
Ts: tosyl
TLC: thin layer chromatography The process according to the invention consists in using 3-tosyloxy-1,2-O-isopropylidenepropane-1,2-diol (II) in an optically pure form in order to introduce the asymmetric carbon C* of the compound (I). The compound (II) in the (R) form is commercially available and the (S) antipode is obtained by known methods. Condensing the compound (II) with a suitably chosen primary amine (III) derived from tryptamine gives the compound (IV)—in which the stereochemistry of C* is preserved: if (R)-3-tosyloxy-1,2-O-isopropylidenepropane-1,2-diol is condensed with (III), the C* of (IV) has the (S) configuration, and if (S)-3-tosyloxy-1,2-O-isopropylidenepropane-1,2-diol is condensed with (III), the C* of (IV) has the (R) configuration (Priority rules, R. S. CAHN, C. INGOLD and V. PRELOG, Angew. Chem. Int. Ed. Eng. (1966), 5, 385).

The reaction scheme is as follows:

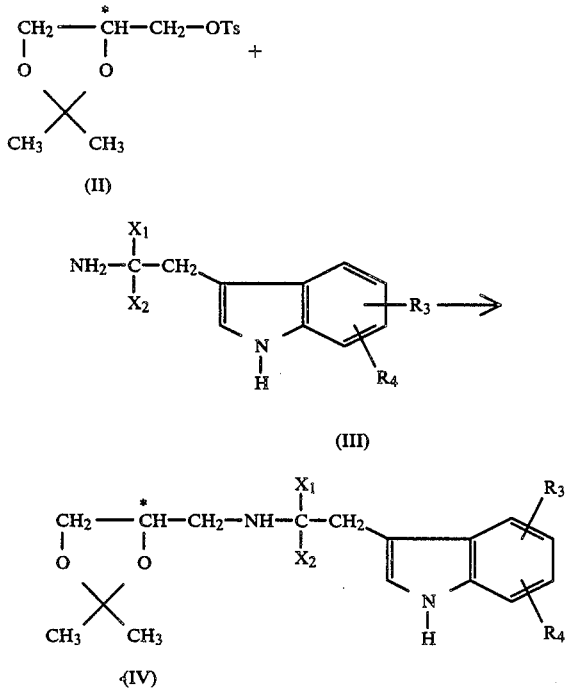

This reaction is performed by heating in an inert solvent. In the reaction, part of the amine (III) is converted to the p-toluenesulfonic acid salt of this amine; if the reaction has been performed in the presence of an excess of the amine (III), the excess (III) is advantageously regenerated by treating the reaction medium with sodium hydroxide.

If the substituents $X_1$ and $X_2$ are different, the amine (III) has a center of asymmetry. In this case, if (IV) is formed from an optically pure isomer of (III), the chirality of the carbon carrying $X_1$ and $X_2$ is preserved and the compound (IV) is optically pure. It is also possible to prepare (IV) from an amine (III) in the racemic form and to separate the epimers in a subsequent step.

Starting from (IV), the following operations are carried out successively and in any order: the hydrolysis of the dioxolan ring in an acid medium and the substitution of the amine functional group by an oxycarbonyl group ROCO, in which R represents a lower alkyl or a benzyl, to form the compound (VI):

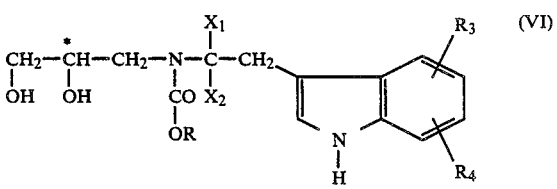

The chirality of C* is preserved in this sequence of reactions. If appropriate, the chirality of C carrying $X_1$ and $X_2$ is also preserved.

Thus, in one embodiment, the dioxolan ring of the compound (IV) is opened by hydrolysis in an acid medium to give the corresponding 1,2-diol (V), after which the amine functional group of (V) is substituted by an oxycarbonyl group ROCO, in which R represents a lower alkyl or a benzyl, such as tert.-butoxycarbonyl (Boc) or methoxycarbonyl, to give (VI).

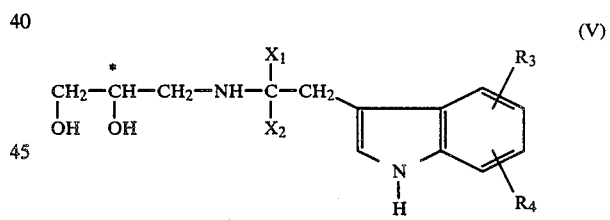

In another embodiment, the amine of the compound (IV) is first substituted by an oxycarbonyl group ROCO to form the compound (IV'), after which the dioxolan ring of (IV') is hydrolyzed in an acid medium to give the compound (VI).

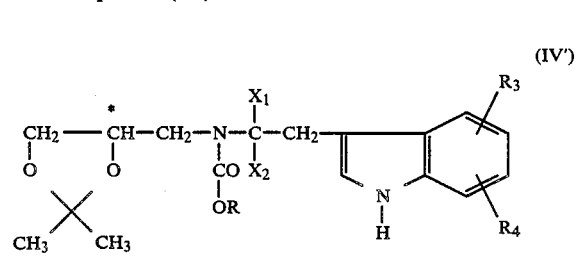

If the compound (VI) is heated in a basic medium, in a water/alcohol mixture or in a non-aqueous solvent such as DMF, the oxazolidinone (VII) is formed:

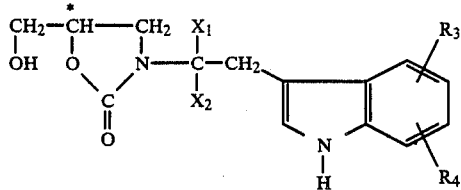

(VII)

The reaction can be performed in a water/alcohol mixture or in a non-aqueous solvent such as DMF. If the reaction is performed in a solvent containing water, the heating must be controlled to prevent the opening of the oxazolidine ring formed.

If appropriate, the indolic nitrogen of one of the compounds (IV') or (VII) can temporarily be selectively protected by a group such as tosyl or mesyl by reaction with tosyl or mesyl chloride in DMF at ordinary temperature.

After esterification of the alcohol functional group of (VII) with tosyl chloride or mesyl chloride in pyridine at ordinary temperature or, preferably, at a temperature of 0° C. or below, the product is reacted with a phenol of the formula (VIII) in the presence of an alkaline agent such as sodium hydroxide, potassium hydroxide, a sodium or potassium alcoholate or sodium hydride, in an appropriate solvent, the phenol having the formula:

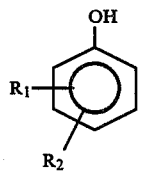

(VIII)

in which $R_1$ and $R_2$ have the meanings indicated above. This gives the compound (IX) in which the chirality of C* and, if appropriate, that of C carrying $X_1$ and $X_2$ are preserved.

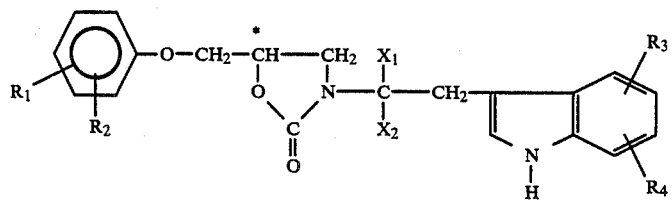

(IX)

The opening of the oxaziddinone (IX) to give the indole derivatives (I) is carried out in a basic medium by heating under reflux in the presence of water, in a suitable solvent such as an alcohol, a glycol, a glycol ether or a dipolar solvent like disulfolan. If the phenol (VIII) carries one or two formyl functional groups capable of reacting with alkaline agents, the said formyl groups can be protected in the form of a dioxolan before the formation of the oxazolidinone (IX). The formyl functional group is then regenerated by methods known in organic chemistry.

If $X_1$ is different from $X_2$, the intermediates (IV), (IV') or (V), (VI), (VII) and (IX) and the compound (I) are optically pure if the amine (III) is optically pure. If the amine (III) is in the racemic form, the compound (IV) is a mixture of epimers. Resolution can be effected after any step of the process, i.e. starting from one of the compounds (IV), (IV'), (V), (VI), (VII) or (IX), or on the compound (I) in the final step.

If appropriate, a pharmaceutically acceptable salt of (I) is then prepared with a mineral or organic acid such as hydrochloric acid, fumaric acid or maleic acid.

Compounds (I) prepared according to the invention can be used to obtain other indole derivatives by performing appropriate reactions on (I). For example, if $R_1$=CHO and $R_2$=H, it is possible to prepare the corresponding oxime of (I), then the cyano derivative and, if appropriate, the corresponding amide derivative of (I).

The process according to the invention can also be applied to the preparation of indole derivatives similar to (I) which carry a variety of substituents on the benzene nucleus and on the indole nucleus. However, if the benzene nucleus carries a functional group capable of reacting with alkaline agents, this functional group must be protected before the formation of the oxazolidinone similar to (IX).

In the process according to the invention, the optically active intermediates (VII) and (IX) are novel.

Thus, the present invention also relates to the 5-hydroxymethyl-3-(2-(indol-3-yl)ethyl)-1,3-oxazolidin-2-one derivatives of the formula:

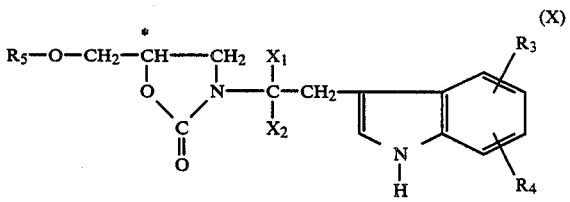

(X)

in which:
the C* atom has the (R) or (S) configuration;
$R_5$ represents a hydrogen atom or a group:

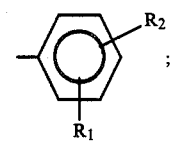

and
$X_1$, $X_2$, $R_1$, $R_2$, $R_3$ and $R_4$ have the meanings indicated above for the compounds of the formula (I).

If $X_1$ is different from $X_2$, the compound (X) has one of the following configurations: (R,R), (R,S), (S,S), (S,R) or the mixture of epimers (R,R)(R,S) or (S,R)(S,S).

One preferred embodiment of the process according to the invention consists in condensing (R)-3-tosyloxy-1,2-O-isopropylidenepropane-1,2-diol with d,l-α-methyltryptamine (III; $X_1$=CH$_3$, $X_2$=$R_3$=$R_4$=H) in order to prepare (2S)-5-hydroxymethyl-3-(2-(indol-3-yl)-1-methylethyl)-1,3-oxazolidin-2-one (VII), with which orthocresol (VIII; R₁=ortho-CH₃, R₂=H) is reacted. This gives (2S)-3-(2-(indol-3-yl)-1-methylethyl)-5-(2-methylphenoxymethyl)-1,3-oxazolidin-2-one (IX), which is separated into the 2 epimers (2S,1′R) and (2S,1′S). Finally, the neutral fumarate of 1-(2-(indol-3-yl)-1-methylethylamino)-3-(2-methylphenoxy)propan-2-ol (I) is prepared in its 2 epimeric forms (2S,1′R) and (2S,1′S).

Another preferred embodiment of the process according to the invention consists in condensing (R)-3-tosyloxy-1,2-O-isopropylidenepropane-1,2-diol with α,α-dimethyltryptamine (III; X₁=X₂=CH₃, R₃=R₄=H) in order to prepare (S)-3-(1,1-dimethyl-2-(indol-3-yl)ethyl)-5-hydroxymethyl-1,3-oxazolidin-2-one (VII), with which 4-hydroxyindole (VIII) is reacted in the form of N-tosyl-4-hydroxyindole. This gives (S)-3-(1,1-dimethyl-2-(indol-3-yl)ethyl)-5-(indol-4-yloxymethyl)-1,3-oxazolidin-2-one (IX). Finally, (S)-3-(1,1-dimethyl-2-(indol-3-yl)ethylamino)-1-(indol-4-yloxy)propan-2-ol is prepared.

The examples which follow illustrate the invention without however implying a limitation.

The optical rotation ($\alpha_D$), expressed in degrees, is measured at 25° C.; the concentration of the product (c) and the solvent used are indicated in brackets. The melting points (m.p.) are measured by the capillary tube method.

The chemical name of the pure optical isomers for which only one center of asymmetry has a known configuration only specifies the configuration of the center defined.

EXAMPLE 1

Neutral fumarate of (2S)-1-(2-(indol-3-yl)-1-methylethylamino)-3-(2-methylphenoxy)propan-2-ol (1)
(2S)-3-(2-(Indol-3-yl)-1-methylethylamino)-1,2-O-isopropylidenepropane-1,2-diol 60 g of (R)(−)-3-tosyloxy-1,2-O-isopropylidenepropane-1,2-diol and 72 g of d,l-α-methyltryptamine (2 equivalents) are heated in 300 ml of benzene for 72 hours. After cooling, the mixture is filtered; the solid recovered is washed with benzene and the organic phases are combined and treated with aqueous sodium carbonate. The organic phase is dried over sodium sulfate, the solvent is then evaporated off under reduced pressure and the oily residue is chromatographed on silica using an ethyl acetate/methanol mixture (7/3; v/v) as the eluent. This gives 57 g of product in the form of an oil.

Yield: 94%;
$\alpha_D = +9.5$ (c=1.85; chloroform).
$C_{17}H_{24}N_2O_2$:
Analysis: Calculated: C=70.80 H=8.39 N=9.71. Found: C=70.69 H=8.60 N=9.67.

The solid collected by filtration is suspended in ethyl acetate and shaken with aqueous sodium hydroxide. 30 g of excess d,l-α-methyltryptamine are thus recovered.
Yield: 83%;
$\alpha_D = 0$.

(2)
(2S)-3-(2-(Indol-3-yl)-1-methylethylamino)propane-1,2-diol

The compound obtained in the previous step (50 g) is heated for 6 hours in 600 ml of a 20% aqueous solution of acetic acid. After cooling, the mixture is left overnight at room temperature and part of the solvent is evaporated off using a water-jet pump until the volume is about 150 ml. Extraction is carried out with ether, a dilute aqueous solution of sodium hydroxide is then added and the aqueous phase is extracted 3 times with ethyl acetate. After washing and drying over sodium sulfate several times, the solvent is evaporated off to give a brown oil.

Weight: 42 g;
Yield: 95%;
$\alpha_D = -8.5$ (c=1.85; chloroform).
$C_{14}H_{20}N_2O_2$:
Analysis: Calculated: C=67.71 H=8.12 N=11.28. Found: C=67.62 H=8.18 N=10.43.

(3)-(2S)-3-(N-Boc-2-(Indol-3-yl)-1-methylethylamino)-propane-1,2-diol

A solution of 43 g of the aminodiol obtained in the previous step and 32.5 g of (Boc)₂O in 200 ml of THF is heated under reflux for 7 hours. After standing overnight at room temperature, the solvent is evaporated off under reduced pressure and the residue is purified by chromatography on silica. The expected compound is eluted in the form of an oil with an ether/methylene chloride mixture (1/1; v/v).

Weight: 41 g;
Yield: 68%;
$\alpha_D = -7.6$ (c=1.1; methanol).
$C_{19}H_{28}N_2O_4$:
Analysis: Calculated: C=65.49 H=8.04 N=8.04. Found: C=64.74 H=7.94 N=7.84.

(4)-(2S)-5-Hydroxymethyl-3-(2-(indol-3-yl)-1-methylethyl)-1,3-oxazolidin-2-one

The compound obtained in the previous step (27 g) is dissolved in 270 ml of ethanol, this being followed by the addition of water and sodium hydroxide to bring the solution to pH 13.5. The mixture is heated at 64° C. for 72 hours. It is then concentrated by evaporation of part of the ethanol using a water-jet pump, and the oxazolidinone is then extracted with methylene chloride (4 times 100 ml). The organic phases are combined and dried over sodium sulfate, the solvent is evaporated off in vacuo and the residue is then purified by chromatography on silica, using pure ethyl acetate as the eluent, to give the expected compound in the form of an oil.

Weight: 17 g;
Yield: 81%;
$\alpha_D = +22.7$ (c=1; methanol).
$C_{15}H_{18}N_2O_3$:
Analysis: Calculated: C=65.67 H=6.56 N=10.20. Found: C=65.03 H=6.49 N=9.87.

(5)
(2S)-3-(2-(Indol-3-yl)-1-methylethyl)-5-(2-methylphenoxymethyl)-1,3-oxazolidin-2-one The compound obtained in the previous step (17 g) is dissolved in 75 ml of pyridine and the solution is then cooled to −5° C. 12 g of tosyl chloride are then added in small portions over a period of 30 minutes and the mixture is kept at 0° C. for 72 hours. It is poured into iced water and extracted 4 times with methylene chloride and the extract is washed with a 2N solution of hydrochloric acid until the pH of the washings is acid, dried and concentrated on a rotary evaporator at 30° C.

This gives an oil (26 g). TLC on silica (eluent: ethyl acetate) reveals the presence of 2 isomers.

1.45 g of sodium are dissolved in 90 ml of methoxyethanol, 6.8 g of orthocresol are added and the mixture is then heated at 120° C. for 20 minutes. When the heating has stopped, the product obtained above (26 g) is added dropwise over a period of 30 minutes and the mixture is heated at 120° C. for 3 hours and then left to return to room temperature overnight. It is poured into iced water and then extracted 5 times with methylene chloride and the organic phase is washed with a 1N solution of sodium hydroxide, dried and concentrated. The oil obtained is chromatographed on a column of silica prepared with an ethyl acetate/pentane mixture (80/20; v/v). Pure ethyl acetate is used as the eluent to give a mixture of the 2 isomers, which are subsequently separated. The crystals which appear in different fractions are filtered off to give 5 g of a mixture rich in the less polar isomer, and the mother liquors are retained. The mixture rich in the less polar isomer is subjected to fractional crystallization from ethyl acetate to give crystals of 95% purity according to NMR.

Weight: 3 g;
$\alpha_D = +83$ (c=1; methanol).

This compound is the expected product in the (2S,1′S) configuration.

The mother liquors are concentrated to give 7.9 g of a mixture rich in the more polar isomer, this mixture being chromatographed on silica using a pentane/ethyl acetate mixture (50/50; v/v) as the eluent.

2.8 g of oil are obtained.
$\alpha_D = +27.2$ (c=1; methanol).

This compound is the expected product in the (2S,1′R) configuration.

(6) Neutral fumarate of (2S,1′S)-1-(2-(indol-3-yl)-1-methylethylamino)-3-(2-methylphenoxy)propan-2-ol (SR 41 410 A)

A suspension of 3.45 g of the less polar isomer isolated in the previous step, in 50 ml of ethanol and 45 ml of 4N sodium hydroxide, is heated under reflux for 72 hours. The solvent is evaporated off, the residue is taken up with 50 ml of water, the mixture is extracted 3 times with methylene chloride and the extract is dried and concentrated. The oil obtained (3.3 g) is placed in 30 ml of hot ethyl acetate and treated with one equivalent of fumaric acid dissolved in the minimum amount of boiling ethanol; the crystals obtained are recrystallized from an ethanol/water mixture (60/40; v/v).

Weight: 1.4 g;
M.p. = 162°–163° C.

The mother liquors from recrystallization are concentrated, treated with sodium hydroxide and then fumaric acid and recrystallized under the same conditions.

Weight: 700 mg;
M.p. = 162°–163° C.;
Total weight of the expected compound: 2.1 g;
Yield: 56%;
$\alpha_D = 0$ (c=1; ethanol/water: 60/40);
Optical rotation measured in polarized light at 400 nm: +7° (c=1; ethanol/water: 60/40; v/v).
$C_{23}H_{28}N_2O_4$:
Analysis: Calculated: C=69.68 H=7.12 N=7.06. Found: C=69.27 H=7.00 N=6.97.

(7) Neutral fumarate of (2S,1′R)-1-(2-(indol-3-yl)-1-methylethylamino)-3-(2-methylphenoxy)propan-2-ol (SR 41 475 A)

A suspension of 1.8 g of the more polar compound (90% enriched) isolated in step 5, in 50 ml of ethanol and 45 ml of 4N sodium hydroxide, is heated under reflux for 72 hours. The solvent is evaporated off, the residue is taken up with 50 ml of water, the mixture is extracted with methylene chloride and the extract is dried and concentrated. The concentrate is chromatographed on a column of silica, using an ethyl acetate/methanol mixture (90/10; v/v) as the eluent, to give 1.5 g of product, which is treated with one equivalent of fumaric acid in an ethyl acetate/methanol mixture (90/10; v/v). The crystals obtained are recrystallized from an ethanol/water mixture (60/40; v/v) to give 1.25 g of the expected compound.

Yield: 64%;
M.p. = 166°–167° C.;
$\alpha_D = -29.2$ (c=0.5; ethanol/water: 60/40; v/v).
$C_{23}H_{28}N_2O_4$:
Analysis: Calculated: C=69.68 H=7.12 N=7.06. Found: C=68.59 H=7.10 N=6.77.

The absolute configurations of the products prepared in step 5 and of the compound SR 41 410 A obtained in step 6 and the compound SR 41 475 A obtained in step 7 were determined relative to the absolute configuration of their enantiomers, the two epimers having an alcohol of opposite configuration (R) prepared from each of the two resolved α-methyltryptamines of known absolute configuration.

The neutral fumarates (2R,1′S) and (2R,1′R) of 1-(2-(indol-3-yl)-1-methylethylamino)-3-(2-methylphenoxy)propan-2-ol were thus prepared according to the procedure described below.

(A) Resolution of α-methyltryptamine (a) (S)(+)-α-Methyltryptamine

A solution of 55.2 g of d-camphorsulfonic acid in the minimum amount of isopropanol is added to a solution of d,l-α-methyltryptamine (40 g) in 300 ml of isopropanol. After standing overnight at room temperature, 76 g of the salt are filtered off; this is recrystallized 4 times from a methanol/isopropanol mixture (1/4; v/v). The salt obtained is dissolved in water, 10 g of sodium hydroxide pellets are then added, the free base is extracted with methylene chloride, the organic phase is dried over sodium sulfate and the solvent is evaporated off. The solid obtained is crystallized by dissolution in methylene chloride followed by the addition of isopropyl ether.

This gives 8 g of (S)(+)-α-methyltryptamine.
Yield: 20%;
M.p. = 122°–123.5° C.;
$\alpha_D = +43.2$ (c=1.05; absolute ethanol).
$C_{11}H_{14}N_2$:
Analysis: Calculated: C=76.26 H=7.57 N=16.17. Found: C=75.56 H=8.11 N=15.44.

(b) (R)(−)-α-Methyltryptamine 25.6 g of d,l-α-methyltryptamine enriched in the (R)(−) epimer are recovered from the mother liquors obtained in the previous step, after treatment with sodium hydroxide. This compound is salified with 58 g of O,O′-bis-p-toluoyltartaric acid. The salt obtained is recrystallized 3 times from 900 ml of an ethanol/water mixture (2/1; v/v). 31 g of salt are isolated in this way and are then recrystallized by dissolution in methylene chloride followed by the addition of isopropyl ether.

7.7 g are obtained.
M.p.=122°-123.5°;
$\alpha_D$=−43 (c=1.0; absolute ethanol).
$C_{11}H_{14}N_2$:
Analysis: Calculated: C=76.26 H=7.57 N=16.17. Found: C=75.50 H=8.08 N=15.97.

(B)
(R)(+)-3-(2-Methylphenoxymethyl)propane-1,2-diol

A solution of the sodium salt of orthocresol is prepared by heating 7 ml of anhydrous methoxyethanol, 460 mg of sodium and 2.16 g of orthocresol under reflux. A solution of 5.72 g of (R)(−)-3-tosyloxy-1,2-O-isopropylidenepropane-1,2-diol in 10 ml of methoxyethanol is added to this solution over a period of 15 minutes and the mixture is heated under reflux for 3 hours. After cooling, water is added and the organic phase is extracted 3 times with hexane. The organic phase is washed twice with a dilute solution of sodium hydroxide and then dried over sodium sulfate and the solvent is evaporated off. This gives 3.3 g of a yellow oil which is dissolved in 16 ml of acetic acid, 4 ml of water are added and the mixture is then heated at 70° C. for 90 minutes. After standing overnight at room temperature, water is added and the mixture is then neutralized slowly by the addition of sodium bicarbonate. The organic phase is extracted with ethyl ether. After washing and then drying over sodium sulfate, the solvent is evaporated off and the residue is crystallized from a methylene chloride/isopropyl ether mixture.

2.2 g are obtained.
M.p.=88° C.; literature: 89°-90° C.;
Optical rotation measured in polarized light at 400 nm=+12.8 (c=5.07; chloroform).

(C)-(S)(+)-3-(2-Methylphenoxymethyl)-1-tosyloxypropan-2-ol

A solution of 5.5 g of the compound obtained in the previous step, in 25 ml of pyridine, is cooled to −13° C. 5.75 g of tosyl chloride freshly recrystallized from hexane are added over a period of 30 minutes. The mixture is kept at 0° C. for 8 days, with occasional stirring. 100 ml of ethyl acetate are then added at 0° C., followed by 150 ml of 20% sulfuric acid. The organic phase is decanted and the residue is extracted 3 times with ethyl acetate. The extracts are combined, washed with an aqueous solution of sodium bicarbonate until the washings are neutral, and then with saline water, and dried over sodium sulfate. Evaporation in vacuo at 50° C. gives 8.5 g of an oil which is purified by chromatography on a column of silica using ether as the eluent.

7.85 g are obtained.
Yield: 78%;
$\alpha_D$ at 26° C.=+12.8 (c=8.39; chloroform).

(D) Neutral fumarate of (2R,1'R)-1-(2-(indol-3-yl)-1-methylethylamino)-3-(2-methylphenoxy)propan-2-ol (SR 41 624 A)

3.4 g of the compound obtained in the previous step and 3.5 g of (R)(−)-α-methyltryptamine prepared in the first step are mixed in 250 ml of benzene and the mixture is heated under reflux for 18 hours. The solvent is evaporated off in vacuo and 250 ml of methylene chloride and then a concentrated solution of sodium hydroxide are added to the residue. The organic phase is decanted and dried over sodium sulfate and the solvent is then evaporated off. The residue is purified by chromatography on a column of silica using an ethyl acetate/methanol mixture (9/10; v/v) as the eluent. This gives 2 g of product in the form of an oil. The salt is prepared in 40 ml of an ether/ethyl acetate mixture (3/1; v/v) containing 0.68 g of fumaric acid.

1.35 g are obtained.
Yield: 29%;
M.p.=162°-163° C.;
$\alpha_D$=0 (c=0.5; ethanol/water:6/4; v/v);
Optical rotation measured in polarized light at 400 nm=−8.2 (c=0.5; ethanol/water:6/4; v/v).
$C_{23}H_{28}N_2O_4$:
Analysis: Calculated: C=69.68 H=7.12 N=7.06. Found: C=69.56 H=7.59 N=6.79.

Neutral fumarate of (2R,1'S)-1-(2-(indol-3-yl)-1-methylethylamino)-3-(2-methylphenoxy)propan-2-ol (SR 41 583 A)

Using the method described above, this compound is obtained from 5.2 g of (S)(+)-α-methyltryptamine and g of (S)(+)-3-(2-methylphenoxymethyl)-1-tosyloxypropan-2-ol. The fumaric acid salt is formed in 45 ml of an ethyl acetate/methanol mixture (2/1; v/v), this being followed by crystallization from ethanol.

1.75 g of the expected compound are obtained.
Yield: 30%;
M.p.=169°-170° C.;
$\alpha_D$=+31.4 (c=1; ethanol/water:6/4; v/v);
Optical rotation measured in polarized light at 400 nm=+81.4 (c=1; ethanol/water: 6/4; v/v).
$C_{23}H_{28}N_2O_4$:
Analysis: Calculated: C=69.68 H=7.12 N=7.06. Found: C=69.89 H=7.06 N=6.97.

EXAMPLE 2

(S)(−)-3-(1,1-Dimethyl-2-(indol-3-yl)ethylamino)-1-(indol-4-yloxy)propan-2-ol ((S)(−)-CM 40441)

(1)
(S)(+)-3-(1,1-Dimethyl-2-(indol-3-yl)ethylamino)-1,2-O-isopropylidenepropane-1,2-diol A mixture of 15.5 g of (R)(−)-3-tosyloxy-1,2-O-isopropylidenepropane-1,2-diol and 20.1 g of α,α-dimethyltryptamine in toluene (250 ml) is heated under reflux for 66 hours. It is cooled to 70° C., 100 ml of 3N sodium hydroxide are added and the mixture is stirred vigorously for 5 minutes and then left to return to room temperature. The solid which precipitates is filtered off. If this is recrystallized twice by dissolution in chloroform and then the addition of the minimum amount of isopropyl ether, 7.5 g of excess amine are recovered (74% of the excess).

The liquors from the first filtration are washed with dilute sodium hydroxide; after drying over magnesium sulfate, the toluene is evaporated off and the residue is chromatographed on silica gel. The expected product is eluted with ethyl acetate and then an ethyl acetate/methanol mixture (95/5; v/v).

This gives a white solid: 11.35 g.
Yield: 69.5%;
$\alpha_D$=+2.18 (c=1.92; chloroform).

A sample is recrystallized by dissolution in isopropyl ether and the addition of the minimum amount of isopropyl ether.
M.p.=100°-102° C.;
$\alpha_D$=+2.21 (c=3.16; chloroform).

$C_{18}H_{26}N_2O_2$:
Analysis: Calculated: C=71.49 H=8.67 N=9.26. Found: C=71.29 H=8.65 N=9.13.

(2)
(S)-3-(1,1-Dimethyl-2-(indol-3-yl)ethylamino)propane-1,2-diol 7.2 g of the compound obtained in the previous step are heated at 80° C. for 7 hours in 130 ml of water containing 20 ml of acetic acid. The mixture is cooled in ice and then rendered alkaline with concentrated sodium hydroxide and extracted 3 times with ethyl acetate; the extract is washed with water and saline water, dried over magnesium sulfate and evaporated. The residue obtained (6.8 g) is crystallized once by dissolution in methylene chloride and the addition of the minimum amount of isopropyl ether. This gives 4.2 g of the expected product.
Yield: 67%;
M.p.=77°–7.79° C.

(3)
(S)-3-(N-Boc-1,1-Dimethyl-2-(indol-3-yl)ethylamino)-propane-1,2-diol

The compound obtained in the previous step (3.5 g) is heated in 120 ml of THF with one equivalent of (Boc)$_2$O (2.9 g) for 3 days. The mixture is evaporated in vacuo and the residue is chromatographed on silica gel using a hexane/ethyl acetate mixture as the eluent.
This gives 1.4 g of the expected product.
Yield: 29%;
Infrared absorption spectrum in methylene chloride:
$\lambda(cm^{-1})$=3560, 3480, 1696, 1680.
$C_{20}H_{30}N_2O_4$:
Analysis: Calculated: C=66.27 H=8.34 N=7.73. Found: C=65.85 H=8.38 N=7.29.

(4)
(S)(+)-3-(1,1-Dimethyl-2-(indol-3-yl)ethyl)-5-hydroxymethyl-1,3-oxazolidin-2-one The compound obtained in the previous step (1.7 g) is dissolved in 30 ml of ethanol, 30 ml of water brought to pH 13.5 by the addition of sodium hydroxide are then added and the mixture is heated at 60° C. for 36 hours. It is neutralized with dilute hydrochloric acid, the ethanol is evaporated off, the residue is extracted with ethyl acetate and the extract is washed with water, dried over magnesium sulfate and evaporated. The solid obtained is chromatographed on silica gel using ethyl acetate as the eluent. After recrystallization by dissolution in methylene chloride and the addition of the minimum amount of isopropyl ether, 477 mg of the expected product are obtained.
Yield: 35%;
M.p.=142°–144° C.;
$\alpha_D$=+27.2 (c=1.14; methanol).
$C_{16}H_{20}N_2O_3$:
Analysis: Calculated: C=66.65 H=6.99 N=9.72 Found: C=66.49 H=6.92 N=9.59.

The same compound can be prepared by a different procedure, which is described below:
1.12 g of the diol obtained in step 3 are heated overnight at 120° C. in 15 ml of DMF, in the presence of 1.1 g of solid potassium carbonate, with magnetic stirring. The solvent is evaporated off at 50° C. under a vane pump vacuum, water is added, the mixture is extracted with 3 volumes of ethyl acetate and the extract is washed once with water and saline water and dried over magnesium sulfate. After evaporation of the solvent, 820 mg of a solid product are isolated. It is purified on a column of silica gel equilibrated in ethyl acetate beforehand.
Elution with the same solvent gives the expected compound in the form of a solid (600 mg) which is homogeneous according to TLC.
Yield: 68%;
$\alpha_D$ of the non-recrystallized compound=+26.5 (c=0.83; methanol).

(5)
(S)(+)-3-(1,1-Dimethyl-2-(indol-3-yl)ethyl)-5-tosyloxymethyl-1,3-oxazolidin-2-one The compound prepared in the previous step (1.155 g) is dissolved in 6 ml of pyridine, one equivalent of tosyl chloride (762 mg) is then added at 0° C. and the mixture is kept in a refrigerator for 3 days. It is poured into iced water and extracted with 4 volumes of methylene chloride and the extract is washed twice with 100 ml of an iced 2N solution of hydrochloric acid and then with water. After drying over sodium sulfate, the solvent is evaporated off; the residue is used as such for the subsequent reaction.

(6)
(S)(+)-3-(1,1-Dimethyl-2-(indol-3-yl)ethyl)-5-((N-tosylindol-4-yl)oxymethyl)-1,3-oxazolidin-2-one 643 mg of N-tosyl-4-hydroxyindole prepared by known methods are dissolved in 4 ml of DMF under nitrogen. 125 mg of 55% sodium hydride are added, the mixture is stirred at room temperature for 15 minutes, 1 g of the tosylate prepared in the previous step, in 6 ml of DMF, is added and then, after stirring for 1 hour at room temperature, the reaction mixture is heated at 50° C. for 90 minutes. It is poured onto ice and extracted with 4 volumes of ethyl acetate and the extract is washed 3 times with a solution of sodium carbonate and then with water and saline water. It is dried over magnesium sulfate and evaporated. The residue is chromatographed on silica gel (twice) using a pentane/ethyl acetate mixture (40/60; v/v) as the eluent. The product is recrystallized from a methylene chloride/methanol mixture.
270 mg are obtained.
Yield: 22%;
$\alpha_D$= +46.5 (c=0.6; chloroform) at 24° C.;
M.p.=141°–143° C.
$C_{31}H_{31}N_3O_5S$:
Analysis: Calculated: C=66.77 H=5.60 N=7.54. Found: C=66.38 H=5.50 N=7.37.

(7)
(S)(+)-3-(1,1-Dimethyl-2-(indol-3-yl)ethyl)-5-((indol-4-yl)oxymethyl)-1,3-oxazolidin-2-one 240 mg of the compound obtained above are heated under reflux in a water/dioxane/ethanol mixture (3/3/7; v/v/v), in the presence of 75 mg of sodium hydroxide, for 48 hours under nitrogen. The organic solvents are evaporated off, the residue is extracted with ethyl acetate and the extract is washed with a solution of sodium carbonate, water and saline water and dried over magnesium sulfate. The oil obtained (187 mg) is chromatographed on silica gel; elution with ethyl acetate gives 127 mg of the expected oxazolidinone. After trituration in a methylene chloride/isopropyl ether mixture, 107 mg are collected.
Yield: 63%;

M.p.=202°-204° C.;
α_D=+56 (c=0.196; chloroform/dimethylformamide:1/1; v/v).
$C_{24}H_{25}N_3O_3$:
Analysis: Calculated: C=71.44 H=6.25 N=10.41. Found: C=70.42 H=6.20 N=10.14.

This compound can be prepared from the product obtained in step (5) without isolation of the N-tosylated derivative of step (6).

643 mg of N-tosyl-4-hydroxyindole are dissolved in 4 ml of anhydrous DMF at 20° C., under nitrogen. 120 mg of 55% sodium hydride are added and the mixture is stirred at room temperature for 30 minutes. 1 g of the tosylate prepared in step 5 is then added and the reaction mixture is stirred for 3 hours at room temperature and then overnight at 50° C. It is poured onto ice, water is added, the mixture is extracted with 4 volumes of ethyl acetate and the extract is washed 3 times with a solution of sodium carbonate and then with water and saline water. The residue is chromatographed on silica gel and a hexane/ethyl acetate mixture (50/50; v/v) is used as the eluent. A foam (900 mg) is isolated which solidifies on the addition of methylene chloride. This foam contains 3 products:

(S)(+)-3-(1,1-dimethyl-2-(indol-3-yl)ethyl)-5-((N-tosylindol-4-yl)oxymethyl)oxazolidin-2-one;

(S)(+)-3-(1,1-dimethyl-2-(N-tosylindol-3-yl)ethyl)-5-((N-tosylindol-4-yl)oxymethyl)-1,3-oxazolidin-2-one; and the expected product.

The 900 mg obtained are dissolved in 2-methoxyethanol (25 ml), 280 mg of NaOH in 10 ml of water are added and the mixture is heated for 4 hours at 80° C., with magnetic stirring. After cooling, water is added, the mixture is extracted with 4 volumes of ethyl acetate and the extract is washed once with a solution of sodium carbonate and then with water and saline water. After drying (MgSO4) and evaporation of the organic solvent in vacuo, a white solid is isolated which is purified by filtration on a column of silica gel using a mixture of pentane and ethyl acetate (40/60; v/v) as the eluent. The non-recrystallized product isolated in this way has the following characteristics:
Weight: 640 mg;
Yield: 67%;
M.p.=193°-202° C.;
α_D=+54.3 (c=0.5; DMF/chloroform:50/50; v/v).

(8) (S)(−)-CM 40441

101 mg of the oxazolidinone obtained in the previous step are heated under reflux in 5 ml of methoxyethanol, 2 ml of 30% sodium hydroxide are added and reflux is maintained for 3 days. The methoxyethanol is evaporated off, water is added and the mixture is rendered acid with a solution of potassium bisulfate and then alkaline with sodium carbonate. After extraction with ethyl acetate followed by drying over sodium sulfate and evaporation, a foam (158 mg) is isolated. This is chromatographed on silica gel using an ethyl acetate/methanol mixture (80/20; v/v) as the eluent. The product is isolated in the form of a foam.
Weight: 67 mg;
Yield: 72%;
α_D=−17.2±1.2 (c=0.46; chloroform).

(9) Hemifumarate of (S)(−)-CM 40441

This salt is prepared by reacting one equivalent of fumaric acid with 905 mg of the compound obtained in the previous step, in absolute ethanol. This gives 586 mg of the expected salt.
M.p.=152°-156° C.;
α_D=−17.6 (c=0.89; dimethylformamide);
Optical rotation measured in polarized light at 400 nm=−44.6 (c=0.89; dimethylformamide).

EXAMPLE 3

(S)(−)-3-(1,1-Dimethyl-2-(indol-3-yl)ethylamino)-1-((indol-4-yl)oxy)propan-2-ol ((S)(−)-CM 40441)

This compound can be prepared according to a variant of the method described in Example 2.

(1)
(S)(+)-3-(1,1-Dimethyl-2-(indol-3-yl)ethylamino)-1,2-O-isopropylidenepropane-1,2-diol This compound is prepared as in Example 2, step 1.

(2)
(S)(+)-3-(1,1-Dimethyl-2-(indol-3-yl)ethyl)-5-hydroxymethyl-1,3-oxazolidin-2-one 3.9 g of methyl chloroformate are added over a period of 5 minutes to a solution of 6 g of the compound obtained in the previous step, in 100 ml of dioxane, kept at 12° C., and the mixture is stirred at 12° C. for 90 minutes. A solution of 5.6 g of potassium carbonate in 15 ml of water is then added and the mixture is stirred for 60 minutes at 10° C. A further 2 g of methyl chloroformate are added and the temperature is then left to rise to about 15°-18° C. 3.5 g of solid potassium carbonate are added and the mixture is stirred for 60 minutes at 20° C. After the addition of a further 1 g of methyl chloroformate, the mixture is stirred for 1 hour at 20° C. and excess potassium carbonate solution is added. The mixture is extracted with 3 volumes of ethyl acetate and the extract is washed with water and saline water, dried over magnesium sulfate and evaporated.

The residue obtained (oil, about 7.4 g) corresponds to 3-(N-methoxycarbonyl-1,1-dimethyl-2-(indol-3-yl)ethylamino)-1,2-O-isopropylidenepropane-1,2-diol.
α_D=+8.6 (c=0.52; methanol).

This residue is placed in 35 ml of methanol and treated with 8 ml of a 0.1N solution of hydrochloric acid at room temperature for 3 hours and then at 40° C. for 2 and a half hours until the starting material has totally disappeared. Aqueous carbonate is added, the methanol is evaporated off on a rotary evaporator at 40° C. in vacuo, the residue is then extracted with 3 volumes of ethyl acetate, the extract is washed with water and saline water and dried over magnesium sulfate and the solvent is evaporated off to give an oil which corresponds to 3-(N-methoxycarbonyl-1,1-dimethyl-2-(indol-3-yl)ethylamino)propane-1,2-diol.
α_D=−36.0 (c=0.39; methanol).

This product (6.4 g) is heated overnight in 100 ml of DMF at 120° C., in the presence of 6.4 g of potassium carbonate, with stirring. The solvent is evaporated off at 40° C. in vacuo on a rotary evaporator. Water is added, the mixture is extracted with 3 volumes of ethyl acetate, the extract is washed with water and saline water and dried over magnesium sulfate and the solvent is evaporated off in vacuo. The expected solid crystallizes and is filtered off to give 2.4 g.
α_D=+27.3 (c=0.68; methanol).

The mother liquors are chromatographed on silica gel; elution with pure ethyl acetate gives a second fraction of the expected product, which is homogeneous according to TLC: 2.61 g.

$\alpha_D = -26.4$ (c=0.76; methanol);

Total yield of the 3 reactions: 87%.

(3)
(S)(+)-3-(1,1-Dimethyl-2-(indol-3-yl)ethyl)-5-tosyloxymethyl-1,3-oxazolidin-2-one 4.93 g of the alcohol obtained in the previous step are dissolved in 29 ml of anhydrous pyridine and 3.44 g of solid tosyl chloride are then added to the solution cooled to $-10°$ C.; after stirring for a few moments, the mixture is kept in a refrigerator for 3 days. It is then poured into a solution of 100 ml of normal hydrochloric acid containing ice, after which it is extracted with 3 volumes of ethyl acetate and the organic solution is washed twice with an iced solution of normal hydrochloric acid and then with water and saline water. After drying over magnesium sulfate and evaporation on a rotary evaporator at 30° C., the expected tosylate is isolated; it is purified by filtration on a column of silica gel equilibrated in methylene chloride beforehand, methylene chloride being used as the eluent. A foam is isolated after evaporation: 6.58 g.

Yield: 90.2%;

$\alpha_D = +42.5$ ($\pm 1$) (c=0.68 to 0.84; chloroform).

(4)
(S)(+)-3-(1,1-Dimethyl-2-(indol-3-yl)ethyl)-5-((N-tosylindol-4-yl)oxymethyl)-1,3-oxazolidin-2-one 643 mg of N-tosyl-4-hydroxyindole are dissolved in 4 ml of anydrous DMF at 20° C., under a nitrogen atmosphere, 120 mg of sodium hydride as a 55% dispersion in oil are added and the mixture is stirred slowly for 30 minutes. 1 g of the product obtained in the previous step is then added and the mixture is stirred at room temperature for 3 hours and then at 50° C. overnight. It is then poured into a water/ice mixture and extracted with 3 volumes of ethyl acetate, the extract is washed with water and saline water and dried over magnesium sulfate and the solvent is evaporated off on a rotary evaporator. The residue is chromatographed on silica gel using a hexane/ethyl acetate mixture (1/1; v/v) and then pure ethyl acetate as the eluents. The first fraction is homogeneous according to TLC (eluent:cyclohexane/ethyl acetate:1/1; v/v) and the second fraction is inhomogeneous according to TLC (eluent:chloroform). 900 mg of the expected product are thus collected.

Yield: 72%.

(5)
(S)(+)-3-(1,1-Dimethyl-2-(indol-3-yl)ethyl)-5-((indol-4-yl)oxymethyl)-1,3-oxazolidin-2-one The 900 mg of the product obtained above are dissolved in 25 ml of 2-methoxyethanol, a solution of 280 mg of sodium hydroxide in 10 ml of water is added and the mixture is stirred at 80° C., under a nitrogen atmosphere, until the starting material has disappeared, i.e. for about 4 hours. It is cooled, water is added, the mixture is extracted with 3 volumes of ethyl acetate and the extract is washed with a solution of sodium carbonate, water and saline water and dried over magnesium sulfate. After evaporation of the solvent on a rotary evaporator, a white solid is isolated: 640 mg.

Yield: 94%.

This product is homogeneous according to TLC. It is not recrystallized.

$\alpha_D = -54.3$ (c=0.23; chloroform/DMF:1/1; v/v);

M.p. = 193°-202° C.

(6) (S)(−)-CM 40441

This product is obtained by following the procedure of Example 2, step 8.

What is claimed is:

1. A process for the stereospecific synthesis of indole compounds of the formula:

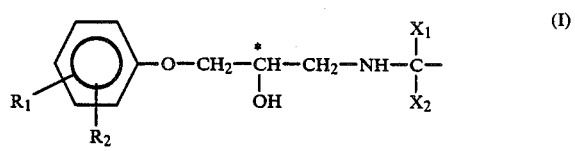

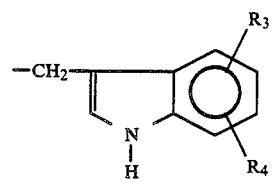

in which:
the configuration of chemical groups attached to the C* atom is (R) or (S);

$X_1$ and $X_2$ each independently denotes a hydrogen atom or a lower alkyl;

$R_1$ and $R_2$ each independently denotes a hydrogen atom, a halogen atom, a lower alkyl, a lower alkoxy or a formyl, or $R_1$ and $R_2$, taken together with the benzene nucleus to which they are bonded, form an optionally substituted bicyclic nucleus selected from the group consisting of:

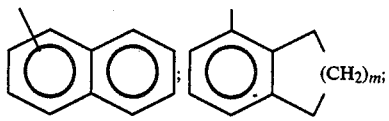

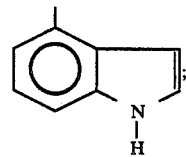

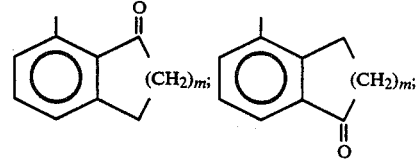

and $R_3$ and $R_4$ each independently denotes a hydrogen atom, a halogen atom, a lower alkyl or a lower alkoxy;

m represents an integer between 1 and 3, and their pharmaceutically acceptable salts with organic or mineral acids, comprising the steps of:

(a) heating 3-tosyloxy-1,2-O-isopropylidenepropane-1,2-diol of formula (II) in an optically pure form with a primary amine of formula (III), in an inert solvent, to give the compound of formula (IV):

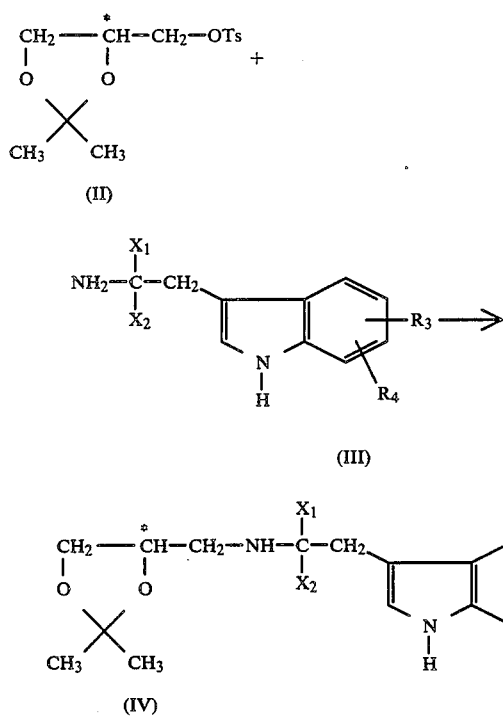

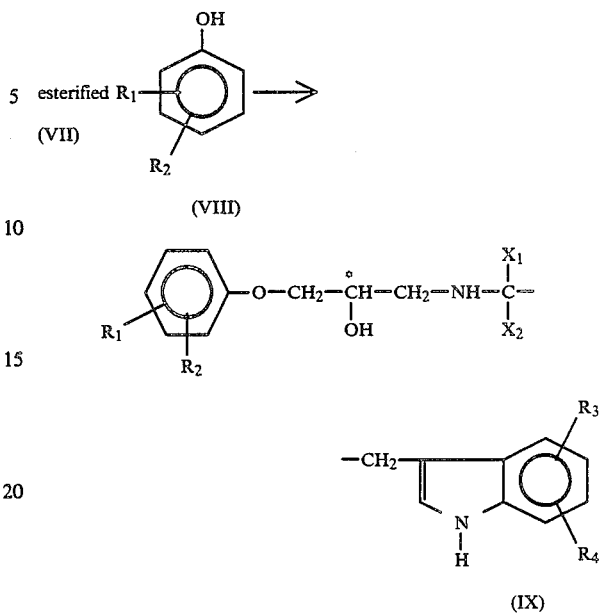

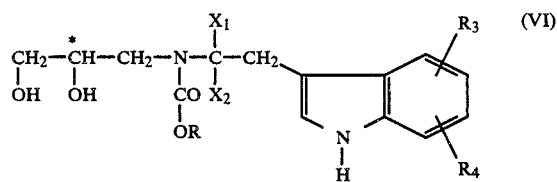

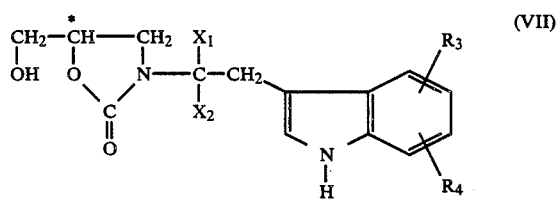

(b) hydrolyzing the dioxolan ring of the compound of formula (IV) in an acid medium and substituting the amine functional group of the said compound with an oxycarbonyl group ROCO, in which R represents a lower alkyl group or a benzyl, to form the compound of formula (VI):

(c) heating compound (IV) in a basic medium in order to prepare the oxazolidinone of formula (VII):

(d) esterifying an alcohol functional group of the compound of formula (VII) with tosyl chloride or mesyl chloride in pyridine;

(e) reacting the compound of formula (VII) esterified in step (d), in the presence of an alkaline agent and in an appropriate solvent, with a phenol of formula (VIII) in order to prepare the compound of formula (IX):

and (f) heating the compound of formula (IX) under reflux in a basic medium, in the presence of water and a solvent, and isolating the resulting compound of formula (I).

2. The process as claimed in claim 1, wherein step (a) is carried out with an optically pure amine of the formula (III) in which $X_1$ is different from $X_2$.

3. The process as claimed in claim 1, wherein step (a) is carried out with an amine of the formula (III) in which $X_1$ is different from $X_2$, in the racemic form, and wherein the mixture of epimers can be resolved after any step of the process or in the final step.

4. The process as claimed in claim 1, wherein the amine of the formula (III) used in step (a) is d,l-α-methyltryptamine and the phenol of the formula (VIII) used in step (e) is orthocresol.

5. The process as claimed in claim 1, wherein the amine of the formula (III) used in step (a) is α,α-dimethyltryptamine and the phenol derivative of the formula (VIII) used in step (e) is 4-hydroxyindole.

6. The process as claimed in claim 1, wherein the oxycarbonyl group ROCO involved in step (b) is a tert.-butoxycarbonyl or methoxycarbonyl group.

7. The process as claimed in claim 1, wherein the heating in step (c) is carried out in a water/alcohol mixture and at a temperature sufficient to prevent oxazolidine ring opening.

8. The process as claimed in claim 1, wherein the heating in step (c) is carried out in a non-aqueous solvent.

9. The process as claimed in claim 1, wherein the alkaline agent involved in step (e) is selected from the group consisting of sodium hydroxide, potassium hydroxide, a sodium or potassium alcoholate and sodium hydride.

10. The process as claimed in claim 1, wherein the solvent of step (f) is selected from the group consisting of an alcohol, a glycol, a glycol ether and a dipolar solvent.

11. A process as claimed in claim 1, further comprising after step (f) the step of converting the resulting compound of formula (I) to one of its pharmaceutically acceptable salts by reaction with a mineral or organic acid.

* * * * *